(12) United States Patent
McDonel et al.

(10) Patent No.: US 10,668,400 B2
(45) Date of Patent: Jun. 2, 2020

(54) QUENCH COLUMN AFTERCOOLER

(71) Applicant: INEOS EUROPE AG, Rolle (CH)

(72) Inventors: Timothy Robert McDonel, Elburn, IL (US); Jay Robert Couch, Naperville, IL (US); Paul Trigg Wachtendorf, Victoria, TX (US); Lani L. Jackson, Naperville, IL (US)

(73) Assignee: INEOS EUROPE AG, Rolle (CH)

( * ) Notice: Subject to any disclaimer, the term of this patent is extended or adjusted under 35 U.S.C. 154(b) by 0 days.

(21) Appl. No.: 16/338,043

(22) PCT Filed: Sep. 26, 2017

(86) PCT No.: PCT/US2017/053371
§ 371 (c)(1),
(2) Date: Mar. 29, 2019

(87) PCT Pub. No.: WO2018/071168
PCT Pub. Date: Apr. 19, 2018

(65) Prior Publication Data
US 2019/0299122 A1  Oct. 3, 2019

(30) Foreign Application Priority Data
Oct. 12, 2016 (CN) .......................... 2016 1 0889386

(51) Int. Cl.
| | | |
|---|---|---|
| *B01D 5/00* | (2006.01) | |
| *B01D 53/00* | (2006.01) | |
| *C07C 253/34* | (2006.01) | |
| *C07C 255/08* | (2006.01) | |
| *F28B 9/08* | (2006.01) | |
| *F28C 1/00* | (2006.01) | |
| *F28C 1/02* | (2006.01) | |
| *F28C 1/16* | (2006.01) | |
| *B01D 53/78* | (2006.01) | |
| *B01D 53/54* | (2006.01) | |
| *B01D 53/14* | (2006.01) | |

(52) U.S. Cl.
CPC .......... *B01D 5/009* (2013.01); *B01D 5/0012* (2013.01); *B01D 53/002* (2013.01); *B01D 53/54* (2013.01); *B01D 53/78* (2013.01); *C07C 253/34* (2013.01); *C07C 255/08* (2013.01); *F28B 9/08* (2013.01); *F28C 1/00* (2013.01); *F28C 1/02* (2013.01); *F28C 1/16* (2013.01); *B01D 5/0027* (2013.01); *B01D 53/1418* (2013.01); *B01D 2251/50* (2013.01)

(58) Field of Classification Search
None
See application file for complete search history.

(56) References Cited

FOREIGN PATENT DOCUMENTS

WO     WO-2015191528 A1 * 12/2015 ........... C07C 255/08

* cited by examiner

*Primary Examiner* — Joseph R Kosack
(74) *Attorney, Agent, or Firm* — David P. Yusko

(57) ABSTRACT

A process for cooling quench effluent includes providing a quench column effluent to a quench column aftercooler condensate; cooling the quench column effluent to provide a quench column aftercooler condensate; and recirculating at least a portion of the quench column aftercooler condensate to the quench column aftercooler at a rate to prevent fouling of the quench column aftercooler.

13 Claims, 2 Drawing Sheets

QUENCH COLUMN AFTERCOOLER

A process is provided for cooling quench column effluent in a quench column aftercooler. More specifically, the process includes recirculating at least a portion of a quench column aftercooler condensate to the quench column aftercooler.

BACKGROUND

Various processes and systems for the manufacture of acrylonitrile and methacrylonitrile are known; see for example, U.S. Pat. No. 6,107,509. Typically, recovery and purification of acrylonitrile/methacrylonitrile produced by the direct reaction of a hydrocarbon selected from the group consisting of propane, propylene or isobutylene, ammonia and oxygen in the presence of a catalyst has been accomplished by transporting the reactor effluent containing acrylonitrile/methacrylonitrile to a first column (quench) where the reactor effluent is cooled with a first aqueous stream, transporting the cooled effluent containing acrylonitrile/methacrylonitrile into a second column (absorber) where the cooled effluent is contacted with a second aqueous stream to absorb the acrylonitrile/methacrylonitrile into the second aqueous stream, transporting the second aqueous stream containing the acrylonitrile/methacrylonitrile from the second column to a first distillation column (recovery column) for separation of the crude acrylonitrile/methacrylonitrile from the second aqueous stream, and transporting the separated crude acrylonitrile/methacrylonitrile to a second distillation column (heads column) to remove at least some impurities from the crude acrylonitrile/methacrylonitrile, and transporting the partially purified acrylonitrile/methacrylonitrile to a third distillation column (product column) to obtain product acrylonitrile/methacrylonitrile. U.S. Pat. Nos. 4,234,510; 3,936,360; 3,885,928; 3,352,764; 3,198,750 and 3,044,966 are illustrative of typical recovery and purification processes for acrylonitrile and methacrylonitrile.

Effluent from the quench column may be cooled further before transporting to other downstream equipment. In one aspect, effluent from a quench is cooled in an indirect contact cooler, called a quench aftercooler (QAC) prior to going to an absorber column. The QAC is typically a vertical, shell-and-tube exchanger with the process effluent flow through the tube side and cooling medium on the shell side. The effluent vapor cools as it travels through the tubes and some organics (primarily acrylonitrile) and water condense, this is called process condensate. Uncondensed vapor exits the bottom of the QAC through a nozzle in the side of the exchanger below the tube sheet. The process condensate exits the bottom of the QAC under level control and is pumped to downstream equipment (absorber or recovery column).

The process may experience a problem of blockage of the QAC tubes that requires periodic shutdown of the plant for mechanical cleaning of the QAC. The blockage is due to gradual buildup of polymer on the inside of the tubes. The polymer is primarily poly-AN. The reason for the polymerization is that some acrylonitrile (AN) condenses on the tubes and this AN monomer is not inhibited, which readily allows polymerization to occur. Furthermore, the quench effluent contains some ammonia which is not removed in the quench, and ammonia reacts with AN in liquid phase condensate to form polymer. The AN polymer is sticky and some can adhere to the inside tube walls and gradually build up leading to blockage of the tubes.

SUMMARY

A process for cooling quench effluent includes cooling a quench column effluent to provide a quench column aftercooler condensate; and recirculating at least a portion of the quench column aftercooler condensate to the quench column aftercooler. The process provides a tube side fouling factor of about 0.0006 $m^{2\circ}$ C. per kcal/hr or less in the quench column aftercooler and a heat transfer coefficient of about 270 kcal/hr per $m^{2\circ}$ C. or more.

A process for cooling quench effluent includes providing a quench column effluent to a quench column aftercooler condensate; cooling the quench column effluent to provide a quench column aftercooler condensate; and recirculating at least a portion of the quench column aftercooler condensate to the quench column aftercooler at a rate to prevent fouling of the quench column aftercooler.

A process for cooling quench effluent, the process includes providing a quench column effluent to a quench column aftercooler; cooling the quench column effluent to provide a quench column aftercooler condensate; and recirculating at least a portion of the quench column aftercooler condensate to the quench column aftercooler at a rate to provide a liquid film thickness of about 0.1 to about 1.1 mm on heat exchanger tubes at an inlet of the quench column aftercooler.

A process for cooling quench effluent includes providing a quench column effluent to a quench column aftercooler; determining a concentration of ammonia in the quench column effluent; and recirculating at least a portion of a quench column aftercooler condensate to the quench column aftercooler when the concentration of ammonia in the quench column effluent is about 20 ppm (by weight) or more.

A process for cooling quench effluent includes providing a quench column effluent to a quench column aftercooler; determining a concentration of acrylonitrile in the quench column effluent; and recirculating at least a portion of a quench column aftercooler condensate to the quench column aftercooler when the concentration of acrylonitrile in the quench column effluent is about 9 weight % or more.

A process for cooling quench effluent includes providing a quench column effluent to a quench column aftercooler, wherein the quench column effluent includes about 20 ppm (by weight) or more ammonia and/or about 9 weight % or more acrylonitrile; and recirculating at least a portion of a quench column aftercooler condensate to the quench column aftercooler.

BRIEF DESCRIPTION OF FIGURES

The above and other aspects, features and advantages of several aspects of the process will be more apparent from the following figures.

Figure 1:
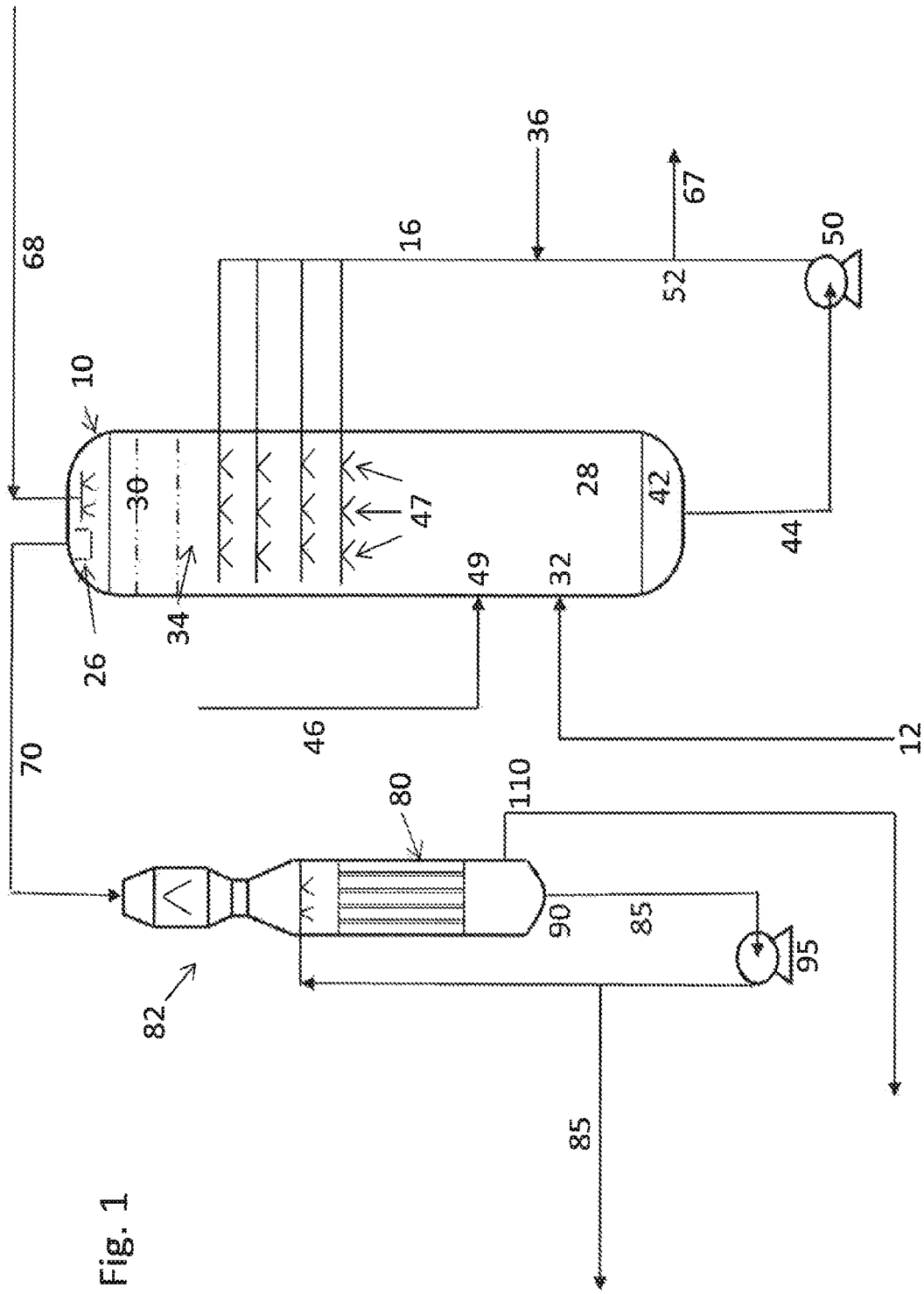
FIG. 1 generally illustrates a quench column and aftercooler.

Corresponding reference characters indicate corresponding components throughout the several views of the drawings. Skilled artisans will appreciate that elements in the figures are illustrated for simplicity and clarity and have not necessarily been drawn to scale. For example, the dimensions of some of the elements in the figures may be exaggerated relative to other elements to help to improve understanding of various aspects. Also, common but well-understood elements that are useful or necessary in a commercially feasible aspect are often not depicted in order to facilitate a less obstructed view of these various aspects.

DETAILED DESCRIPTION

The following description is not to be taken in a limiting sense, but is made merely for the purpose of describing the general principles of exemplary embodiments. The scope of the invention should be determined with reference to the claims.

Quench Column and Quench Column Aftercooler

As shown in FIG. 1, the quench column 10 includes a first portion 28 and a second portion 30, the first portion 28 being located below the second portion 30. The first portion 28 of the quench column 10 includes an inlet 32 configured to receive a gas stream or reactor effluent 12. The gas stream or reactor effluent 12 may include acrylonitrile and ammonia. The second portion 30 of the quench column 10 includes a multi-level spray system 34 that is configured to receive an aqueous stream or quench liquid 16. The aqueous stream or quench liquid 16 may include an acid 36.

Quench liquid 16 may include effluent or quench column bottoms stream exiting bottom 42 of the quench column 10 and through line 44. In an aspect, effluent or quench column bottoms stream may include a concentration of ammonium sulfate of about 45% by weight or less, in another aspect, about 10 to about 25% by weight, and in another aspect, about 15 to about 21% by weight.

Water may be added via line 46 to the quench column 10 through an inlet 49, or otherwise may be added to the quench liquid 16 or elsewhere in the liquid recycle loop formed by streams 16 and 44. Water may also be added to the quench column 10 via a line 68. In this aspect, the quench column may be any type of quench column known in the art, and the quench column may include packing or trays.

Quench liquid 16 may be circulated through a line 44 and back to the quench column using a pump 50. In this aspect, the quench column may include multiple return lines. An exit stream 67 may be withdrawn as part of the quench column bottoms stream exiting through a line 44, in order to maintain a relatively constant mass flow in the liquid recycle loop by offsetting added liquid. An exit stream 67 removes formed neutralization reaction products (e.g., ammonium sulfate) and is also useful for preventing the accumulation of unwanted products in the liquid recycle loop, such as corrosion products. The exit stream 67 may be drawn from line 44 at a discharge point 52.

In an aspect, each nozzle 47 of the spray system 34 may be configured to downwardly spray a hollow cone spray of the quench liquid 16, wherein each hollow cone spray defines a center equidistant from the walls of the hollow cone spray. In an aspect, the nozzles of each spray bar may be spaced so that a portion of a first hollow cone spray of quench liquid from a first nozzle of the first spray bar overlaps with a portion of a second hollow cone spray of quench liquid from a second nozzle of the first spray bar to provide an overlap of the quench liquid.

In another aspect, the quench column may include packed sections of multiple trays in place of multi-level spray system 34. In this aspect, quench liquid 16 is circulated to the quench column above and/or below the packed or tray section of the column.

Cooled effluent gas containing acrylonitrile (including co-products such as acetonitrile, hydrogen cyanide, ammonia and other impurities) along with mist may then rise up from the multi-level spray system 34 to the mist eliminator 26. The mist eliminator 26 is configured to remove mist from the cooled effluent gas. The mist eliminator 26 is located downstream of the second portion 30 of the quench column 10. The mist eliminator 26 may include a water spray system (not shown). The water spray system is configured to spray water to a surface of the mist eliminator 26, wherein collection of droplets is reduced and formation of polymer and corresponding fouling on surfaces of the mist eliminator 26 is reduced.

The quenched or cooled effluent gas that includes acrylonitrile (including co-products such as acetonitrile, hydrogen cyanide, ammonia and other impurities), after passing through mist eliminator 26, may exit quench column 10 as a gas stream 70. In one aspect, the quench column effluent is the gas stream 70.

A gas stream 70 may be sent to one or more entrainment separators 82 and one or more quench column aftercoolers 80. The process may include the use of quench column aftercoolers, for example, such as shell and tube, finned tube, box type, plate type, spiral type, and double pipe type. Condensate 85 may be removed from the quench column after cooler 80 at outlet 90. The process further includes conveying condensate 85 via pump 95 back to the quench column aftercooler 80. A portion of the condensate 85 may be sent to downstream equipment such as an absorber or recovery column (not shown). The pH of the condensate 85 is measured prior to entering downstream equipment. Process stream 110 is a vapor effluent from the aftercooler 80 which may be sent to an absorber.

Operation without Recirculation

Figure 2:
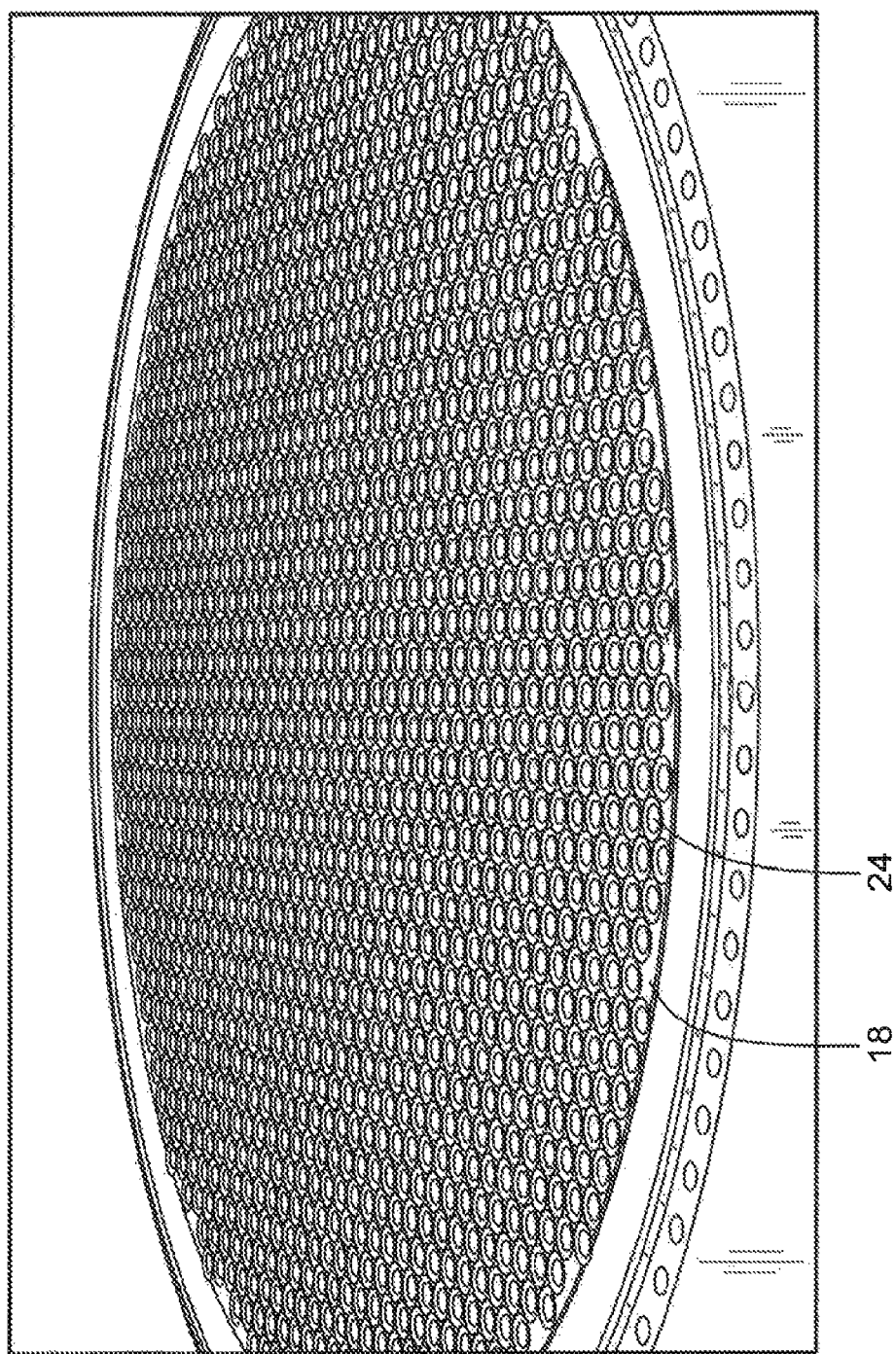
FIG. 2 illustrates a quench aftercooler top tube sheet.

FIG. 2 is a top perspective view of inlet tube sheet 18 located in a quench column aftercooler. Inlet tube sheet 18 may include a plurality of tube inlets 24. Quench column effluent vapor condenses and forms a quench column aftercooler condensate. The quench column effluent vapor may include acrylonitrile together with co-products and impurities. In this aspect, the quench column effluent vapor may include acrylonitrile, hydrogen cyanide, ammonia and other impurities. In this aspect, the quench column effluent vapor has about 9 to about 13 weight % acrylonitrile, and in another aspect, about 11 to about 12 weight % acrylonitrile. The quench column effluent vapor may also contain about 1.0 to about 1.5 weight % hydrogen cyanide, and about 5 to about 200 ppm (by weight) ammonia. The quench column aftercooler condensate includes primarily water and some acrylonitrile, as well as lesser amounts of other components such as acetonitrile, hydrogen cyanide, acrylic acid.

As quench column effluent vapor initially enters the tube sheet 18 through tube inlets 24, surfaces of cooling tubes are continually wetted with the first droplets of condensed vapor. As those first liquid droplets continue to flow down the tubes, that area of wetted tube surface may become temporarily dry until further condensation occurs in that area from continued flow of quench column effluent vapor. The continuous wetting and drying allows for a gradual deposition of polymer on the surfaces of the cooling tubes. In this aspect, some polymerization occurs in liquid droplets and some solid polymer is left on the cooling tube surface when that wetted cooling tube surface dries. Quench effluent at the cooling tube inlets will have a temperature of about 60 to about 90° C.

An increase in droplet formation and droplet size and a decrease in tube surface drying occur further down the cooling tube surface as the distance from the tube inlet 24 increases. As the distance from the tube inlet 24 continues to increase, enough condensation and droplet formation occurs so that liquid is flowing down the cooling tube wall and the cooling tube wall is substantially covered by a liquid film. In this aspect, polymer is continually washed down from the cooling tube surface, resulting in minimal build-up of solid polymer on the cooling tube wall.

To further illustrate, it has been found that for QAC operation without recycle, the liquid film thickness at the very top of the tubes is essentially nil, as almost no condensation has yet occurred. Midway down the tubes, the liquid film thickness is on the order of 0.1 to 0.15 mm. At the bottom of the tubes, the liquid film thickness is on the order of 0.25 to 0.3 mm. Furthermore, it has been found that fouling in the QAC occurs in the upper half of the tubes, with very little fouling in the bottom half of the tubes.

Operation with Recirculation

In one aspect, a portion of quench column aftercooler condensate is recirculated to the quench column aftercooler. FIG. 2 is a top perspective view of inlet tube sheet 18 of a quench column aftercooler. Inlet tube sheet 18 may include a plurality of tube inlets 24. Liquid covers the top of tube sheet 18 and flows into tube sheet inlets 24 and down into the cooling tubes. The tube sheet 18 and cooling tubes are substantially wetted at the tube sheet inlet 24 and down the cooling tubes. Condensation occurs as effluent vapor flows down the tube. Liquid film thickness on the surface of the cooling tube increases as the distance from the tube sheet inlet 24 increases. Substantial wetting of the entire surface of the cooling tubes allows for continuous washing down of the cooling tube surface and minimal build-up of solid polymer on the surface of the cooling tubes.

In another aspect, the process includes recirculating at least a portion of the quench column aftercooler condensate to the quench column aftercooler at a rate to prevent fouling of the quench column aftercooler. In this aspect, quench column aftercooler condensate is recirculated to the quench column aftercooler at a recirculation or recycle rate of about 0.3 to about 10, in another aspect, about 0.3 to about 3, in another aspect, about 1 to about 3, and in another aspect, about 0.3 to about 1. As used herein, "recycle ratio" or "recycle rate" means a liquid recycle 85 molar flow rate divided by to quench effluent vapor 70 molar flow rate.

The process provides a tube side fouling factor of about 0.0006 $m^{2\circ}$ C. per kcal/hr or less in the quench column aftercooler, in another aspect, about 0.0005 $m^{2\circ}$ C. per kcal/hr or less, and in another aspect, about 0.0004 $m^{2\circ}$ C. per kcal/hr or less. The process provides a rate of change of tube side fouling factor in the quench column aftercooler of about 0.00002 $m^{2\circ}$ C. per kcal/hr/month or less.

In accordance with the process, recirculation rates and fouling factor are controlled to provide a heat transfer coefficient of about 270 kcal/hr per $m^{2\circ}$ C. or more, in another aspect, about 278 kcal/hr per $m^{2\circ}$ C. or more, and in another aspect, about 285 kcal/hr per $m^{2\circ}$ C. or more. The process provides a rate of change of heat transfer coefficient of about 5 kcal/hr per $m^{2\circ}$ C./month or less.

In another aspect, quench column aftercooler condensate is recirculated to the quench column aftercooler at a rate to provide and maintain liquid film on an entire surface of the tubes. In this aspect, quench column aftercooler condensate is recirculated to the quench column aftercooler at a rate to provide a liquid film thickness at the top of the tubes of about 0.1 to 0.15 mm up to about 1.0 to 1.1 mm on heat exchanger tubes (at the tube inlet) in the quench column aftercooler, in another aspect, about 0.1 to 0.15 mm up to about 0.45 to 0.5 mm, and in another aspect, in about 0.1 to 0.15 mm up to about 0.2 to 0.25 mm.

The liquid film thickness was estimated based on the per tube flow rates for the liquid and gas, with the liquid segregated to an annular region at the tube wall and the gas flowing through the turbulent core. The liquid shear stress and velocity in the annular region was calculated for laminar flow, using correlations given by Bird, Stewart and Lightfoot. The gas phase shear stress was calculated using the Blasius equation. The film thickness was found by equating the liquid and vapor velocity and shear stress at the interface of the liquid and gas.

As shown in the following calculated values (assuming clean feed with no fouling), as the recycle rate increases and the film thickness increases, the heat transfer coefficient decreases.

| Recycle Rate | Film Thickness (mm) | Heat Transfer Coefficient (kcal/hr per $m^2$ ° C.) |
|---|---|---|
| 0 | 0.124 | 511.3 |
| 0.1 | 0.155 | 490 |
| 0.3 | 0.221 | 456 |
| 1 | 0.335 | 408 |
| 3 | 0.604 | 327 |
| 10 | 1.209 | 225 |

As shown in the following calculated values (assuming a normal feed with fouling), as the recycle rate increase the fouling factor decreases. The heat transfer coefficient increases at recycle rates of 0.1 to 3 as compared to a recycle rate of 0. Effect of recycle rate on quench column inlet temperature is indicated.

| Recycle Rate | Fouling Factor tube side + Fouling Factor shell side | Heat Transfer coefficient (kcal/hr per $m^2$ ° C.) | Inlet Temperature ° C. |
|---|---|---|---|
| 0 | 0.0017 | 271 | 84.0 |
| 0.1 | 0.00127 | 302 | 83.6 |
| 0.3 | 0.0004 | 386 | 83.0 |
| 1 | 0.0004 | 351 | 80.5 |
| 3 | 0.0004 | 289 | 73.5 |
| 10 | 0.0004 | 206 | 58.5 |

In this aspect, a recycle rate of about 0.1 to about 1 provides a fouling factor of about 0.0012 to about 0.0004 $m^{2\circ}$ C. per kcal/hr and a heat transfer coefficient of about 300 to about 400 kcal/hr per $m^{2\circ}$ C. In another aspect, a recycle rate of about 0.3 to about 1 provides a fouling factor of about 0.0004 $m^{2\circ}$ C. per kcal/hr and a heat transfer coefficient of about 390 to about 350 kcal/hr per $m^{2\circ}$ C.

In one aspect, the process includes recirculating at least a portion of a quench column aftercooler condensate to the quench column aftercooler when the concentration of ammonia in the quench column effluent is about 20 ppm (by weight) or more, in another aspect, about 50 ppm (by weight) or more, and in another aspect, about 100 ppm (by weight) or more. In a related aspect, the process includes recirculating at least a portion of a quench column aftercooler condensate to the quench column aftercooler when the concentration of acrylonitrile in the quench column effluent is about 9 weight % or more, in another aspect, about 10 weight % or more, and in another aspect, about 11 weight % or more. In this aspect, the process may include adjusting the recycle rate based on centration of ammonia and/or acrylonitrile in the quench column effluent.

Recycle rates may be adjusted based on ammonia concentration in the quench column effluent as set forth below.

| Ammonia Concentration in Quench Column Effluent | Recycle Rate |
| --- | --- |
| 20 to 100 ppm (by weight) | 0.3 to 1.0 |
| Greater than 100 ppm (by weight) | 1.0 to 3.0 |

Spraying of the Tube Sheet

In one aspect, the process includes providing quench column aftercooler condensate to the tube sheet. The process may include providing quench column aftercooler condensate to the tube sheet with or without the use of a spray nozzle. The process is more effective in reducing fouling when the tube sheet in the quench column aftercooler is completely covered with a spray of the quench column aftercooler condensate. In this aspect, quench column aftercooler condensate may be conveyed to the tube sheet using one or more spray nozzle, such as for example a nozzle providing a full cone spray nozzle, or a nozzle providing a hollow cone spray pattern.

In order to achieve full coverage with a single spray nozzle having a spray angle of SA degrees, the location of the spray nozzle should be centered at a distance H meters above the tube sheet with a diameter of D meters, according to the formula: H=(D/2)/tangent (SA/2). If the spray nozzle is located at a lesser distance, then the spray liquid will not cover the entire tube sheet. If the spray nozzle is located at a greater distance, then some of the spray liquid will impact on the wall of the QAC inlet channel and spray coverage will not be ideal. Depending on the geometry of the QAC inlet channel and the quench effluent piping, it may be the case that it is difficult to properly locate a single spray nozzle to achieve the desired full coverage of the tube sheet. A further complication in the choice of location of a single spray nozzle is that in practice the vapor flow of the quench effluent deflects the liquid spray downward, and higher flow rates give higher deflection. So the optimum location of a single spray nozzle may be different for different operating scenarios.

In one aspect, the QAC condensate may be conveyed to the tube sheet through multiple spray nozzles, for example multiple full cone spray nozzles located equidistant above the tube sheet. The distances between the spray nozzles are set so that there is overlap of the sprays from adjacent spray nozzles. Spray nozzles may be angled to effect spray coverage of the tube sheet. For example, the nozzle may be perpendicular to the tube sheet and up to about a 60° angle from perpendicular to the tube sheet. In one aspect, an outlet of the spray nozzles is about 0.5 to about 1 meter from a surface of the tube sheet, in another aspect, about 0.6 to about 0.9 meters, and in another aspect, about 0.7 to about 0.8 meters.

Inhibitor Addition

In one aspect, an inhibitor is added to the quench column aftercooler condensate before the quench column aftercooler condensate contacts the tube sheet. Inhibitors are effective for preventing polymerization. In this aspect, the inhibitor is selected from the group consisting of hydroquinone, methylhydroquinone, hydroxy-TEMPO, nitro phenols such as DNBP (2,4-dinitro-6-sec-butyl phenol), phenylene diamine and mixtures thereof.

pH Adjustment

In one aspect, the process includes maintaining, and optionally adjusting optimum pH levels of the quench column aftercooler condensate. Maintenance of pH within a defined range provides reduced corrosiveness and allows for use of a wider range of materials of construction in process equipment. In this aspect, the process includes adding mildly alkaline compounds to the quench column aftercooler condensate to provide a pH of about 6 to about 7. Sodium carbonate is preferred due to its low cost and ready availability, but other mildly alkaline compounds may also be used, including alkali metal carbonates and alkali earth metal carbonates and bicarbonates; ammonium carbonate, bicarbonate, or carbamate; alkylene diamines, such as ethylene diamine, propylene diamine, hexamethylene diamine, and the like, and mixtures thereof. In one aspect, the additive to control pH is added to the quench column aftercooler condensate before the quench column aftercooler condensate contacts the quench column aftercooler.

While the invention herein disclosed has been described by means of specific embodiments, examples and applications thereof, numerous modifications and variations could be made thereto by those skilled in the art without departing from the scope of the invention set forth in the claims.

What is claimed is:

1. A process for cooling quench effluent, the process comprising:
   providing a quench column effluent to a quench column aftercooler;
   cooling the quench column effluent to provide a quench column aftercooler condensate; and
   recirculating at least a portion of the quench column aftercooler condensate to the quench column aftercooler at a rate to provide a liquid film thickness of about 0.1 to about 1.1 mm on heat exchanger tubes in the quench column aftercooler.

2. The process of claim 1 wherein the portion of the quench column aftercooler condensate is recirculated to the quench column aftercooler at a rate of about 0.3 to about 1.

3. The process of claim 1 wherein the quench column effluent includes about 20 ppm (by weight) or more ammonia and/or about 9 weight % or more acrylonitrile.

4. The process of claim 3 wherein the quench column effluent includes about 20 ppm (by weight) to about 100 ppm (by weight) ammonia.

5. The process of claim 2 wherein an inhibitor is added to the quench column aftercooler condensate before the quench column aftercooler condensate contacts the heat exchanger tubes.

6. The process of claim 5 wherein the inhibitor is selected from the group consisting of hydroquinone, methylhydroquinone, hydroxy-TEMPO, nitro phenols such as DNBP (2,4-dinitro-6-sec-butyl phenol), phenylene diamine and mixtures thereof.

7. The process of claim 1 wherein the quench column aftercooler condensate is maintained, and optionally adjusted to a pH of about 6 to about 7.

8. The process of claim 7 wherein an additive to control ph is added to the quench column aftercooler condensate before the quench column aftercooler condensate contacts the quench column aftercooler.

9. The process of claim 8 wherein the additive to control pH is selected from the group consisting of sodium carbonate, alkali metal carbonates, alkali earth metal carbonates and bicarbonates, ammonium carbonate, bicarbonate, carbamate, ethylene diamine, propylene diamine, hexamethylene diamine and mixtures thereof.

10. The process of claim 1 wherein the process provides a rate of change of tube side fouling factor in the quench column aftercooler of about 0.00002 $m^2$ ° C. per kcal/hr/month or less.

11. The process of claim 1 wherein the process provides a tube side fouling factor in the quench column aftercooler of about 0.0006 m$^2$ ° C. per kcal/hr or less.

12. The process of claim 1 wherein the process provides a heat transfer coefficient of about 270 kcal/hr per m$^2$ ° C. or more.

13. The process of claim 1 wherein the process provides a rate of change of heat transfer coefficient of about 5 kcal/hr per m$^2$ ° C/month or less.

\* \* \* \* \*